(12) United States Patent
Ohrbom et al.

(10) Patent No.: US 6,362,285 B1
(45) Date of Patent: Mar. 26, 2002

(54) CURABLE COATING COMPOSITIONS CONTAINING CARBAMATE FUNCTIONAL REACTIVE ADDITIVES

(75) Inventors: Walter H Ohrbom, Hartland Township; Paul J. Harris, West Bloomfield, both of MI (US)

(73) Assignee: BASF Corporation, Southfield, MI (US)

( * ) Notice: Subject to any disclaimer, the term of this patent is extended or adjusted under 35 U.S.C. 154(b) by 0 days.

(21) Appl. No.: 09/464,309

(22) Filed: Dec. 15, 1999

(51) Int. Cl.[7] .......................... C09D 201/02; C09D 7/00
(52) U.S. Cl. .................... 525/330.5; 525/375; 525/162
(58) Field of Search .............................. 525/330.5, 375, 525/162

(56) References Cited

U.S. PATENT DOCUMENTS

| | | | |
|---|---|---|---|
| 2,979,514 A | 4/1961 | O'Brien et al. .......... 260/340.2 |
| 3,479,328 A | 11/1969 | Nordstrom ................. 260/86.1 |
| 3,674,838 A | 7/1972 | Nordstrom ................. 260/482 |
| 4,126,747 A | 11/1978 | Cowherd, III et al. | |
| 4,279,833 A | 7/1981 | Culbertson et al. | |
| 4,340,497 A | 7/1982 | Knopf | |
| 4,484,994 A | 11/1984 | Jacobs, III et al. ......... 204/181 |
| 4,520,167 A | 5/1985 | Blank et al. ................. 525/131 |
| 4,758,632 A | 7/1988 | Parekh et al. ............... 525/383 |
| 4,814,382 A | 3/1989 | Hoy et al. | |
| 4,977,231 A | 12/1990 | McVay et al. | |
| 5,115,015 A | 5/1992 | Richey, Jr. et al. ......... 524/507 |
| 5,158,808 A | 10/1992 | Hoy et al. | |
| 5,336,566 A | 8/1994 | Rehfuss | |
| 5,512,639 A | 4/1996 | Rehfuss et al. | |
| 5,552,497 A | 9/1996 | Taylor et al. | |
| 5,593,733 A | 1/1997 | Mayo | |
| 5,646,214 A | 7/1997 | Mayo | |
| 5,714,549 A | 2/1998 | Wu et al. | |
| 5,719,237 A | 2/1998 | Rehfuss et al. | |
| 5,726,254 A | 3/1998 | Wu et al. | |
| 5,744,550 A | 4/1998 | Menovcik et al. | |
| 5,866,259 A | 2/1999 | Harris et al. .............. 428/424.4 |
| 5,872,195 A | 2/1999 | Green et al. ................. 525/481 |

FOREIGN PATENT DOCUMENTS

| | | | |
|---|---|---|---|
| CA | 1295767 | 2/1992 | ............ C09D/7/12 |
| DE | 198 24 656 A1 | 12/1998 | ......... C07C/271/18 |
| EP | WO 87/00851 | 2/1987 | ............ C09D/7/12 |
| EP | WO 88/02766 | 4/1988 | ............ C09D/7/00 |
| EP | 0 680 988 A | 11/1995 | ........... C08G/71/00 |
| EP | 0767 226 A | 4/1997 | ......... C09D/201/00 |
| EP | 0 780 455 A | 6/1997 | ......... C09D/201/06 |
| EP | 0 889 101 A2 | 1/1999 | ............ C09D/5/44 |
| EP | WO 99/33915 | 7/1999 | ............ C08L/33/14 |
| EP | WO 00 37572 A | 6/2000 | ............ C09D/5/44 |
| EP | WO 00 37573 A | 6/2000 | ............ C09D/5/44 |

OTHER PUBLICATIONS

International Search Report for PCT/US 00/27598.
International Search Report for PCT/US 00/28047.
International Search Report for PCT/US 00/27128.
International Search Report for PCT/US 00/28034.
U.S. application No. 08/333,804, Filed Nov. 3, 1994, Walter Ohrbom, Curable coating compositions containing carbamate resin.

*Primary Examiner*—D. R. Wilson
(74) *Attorney, Agent, or Firm*—Mary E. Golota

(57) ABSTRACT

The invention thus provides a curable coating composition comprising (A) a polymer resin comprising active hydrogen-containing functional group other than carbamate, (B) a curing agent having groups that are reactive with said functional groups on (A), and (C) a reactive additive comprising at least one compound having a molecular weight of from 131 to 2000 and comprising at least one β-hydroxy primary carbamate group and at least one alkyl group selected from the group consisting of straight chain alkyl groups of more than 10 carbons, branched alkyl groups of from 5 to 30 carbons, and mixtures thereof, wherein one or both of (A) and (B) comprise groups that are reactive with the primary carbamate group of (C). The invention also provides a method of making a preferred embodiment of the reactive additive (C) and the reactive additive (C).

11 Claims, No Drawings

CURABLE COATING COMPOSITIONS CONTAINING CARBAMATE FUNCTIONAL REACTIVE ADDITIVES

FIELD OF THE INVENTION

The instant invention relates to coating compositions comprising reactive additives. In particular, the invention provides coating compositions comprising a reactive additive comprising at least one compound having a molecular weight of from 131 to 2000 and at least one primary carbamate group and at least one alkyl group selected from the group consisting of straight chain alkyl groups of more than 10 carbons, branched alkyl group of from 5 to 30 carbons, and mixtures thereof.

BACKGROUND OF THE INVENTION

Curable coating compositions such as thermoset coatings are widely used in the coatings art. They are often used for topcoats in the automotive and industrial coatings industry. Color-plus-clear composite coatings are particularly useful as topcoats where exceptional gloss, depth of color, distinctness of image, or special metallic effects are desired. The automotive industry has made extensive use of these coatings for automotive body panels. Color-plus-clear composite coatings, however, require an extremely high degree of clarity in the clearcoat to achieve the desired visual effect. High-gloss coatings also require a low degree of visual aberrations at the surface of the coating in order to achieve the desired visual effect such as high distinctness of image (DOI).

As such, these coatings are especially susceptible to a phenomenon known as environmental etch. Environmental etch manifests itself as spots or marks on or in the finish of the coating that often cannot be rubbed out.

It is often difficult to predict the degree of resistance to environmental etch that a high gloss or color-plus-clear composite coating will exhibit. Many coating compositions known for their durability and/or weatherability when used in exterior paints, such as high-solids enamels, do not provide the desired level of resistance to environmental etch when used in high gloss coatings such as the clearcoat of a color-plus-clear composite coating.

Many compositions have been proposed for use as the clearcoat of a color-plus-clear composite coating, such as polyurethanes, acid-epoxy systems and the like. However, many prior art systems suffer from disadvantages such as coatability problems, compatibility problems with the pigmented basecoat, solubility problems. Moreover, very few one-pack coating compositions have been found that provide satisfactory resistance to environmental etch, especially in the demanding environment of automotive coatings.

Many curable coating compositions utilize a hydroxy-functional polymer resin such as a hydroxy-functional acrylic and a curing agent such as an aminoplast. These coating compositions suffer from environmental etch in certain topcoat applications. In spite of this, it is often desirable to use coatings based on hydroxy-functional or other active hydrogen-functional resins, as there exists a great deal of experience with these coatings, and many multilayer coating systems have incorporated this chemistry into one or more of the layers. It is also desirable to use such coatings for various applications such as basecoat and primer to provide durable coatings. It is especially desirable to utilize such coating compositions in high gloss topcoats, such as the clearcoat of a color-plus-clear composite coating, while also providing resistance to environmental etch.

U.S. Pat. Nos. 4,814,382, 5,114,015, and 5,158,808 describe the use of certain N-alkyl carbamate compounds as reactive diluents in coating compositions having OH-functional curable polymer resins. These compounds, however, may require excessively high catalyst or temperature levels in order to fully react into the crosslink matrix during cure of the film.

WO 87/00851 describes the use of certain reactive carbamate derivatives in an effort to minimize the emission of volatile organic compounds (VOC). U.S. Pat. No. 5,744,550 describes the use of primary carbamate additives. However, further reductions in VOC are desirable without loss of desirable performance properties such as etch resistance and the like.

SUMMARY OF THE INVENTION

It has been surprisingly discovered that certain primary carbamate reactive additives provide advantages over the prior art. In particular, it has been found that the incorporation of a particular reactive additive provides improved sprayability at a given nonvolatile level and advantageous resistance to environmental etch. The reactive additive comprises at least one compound having a molecular weight of from 131 to 2000 and comprising at least one β-hydroxy primary carbamate group and at least one alkyl group selected from the group consisting of straight chain alkyl groups of more than 10 carbons, branched alkyl groups of from 5 to 30 carbons, and mixtures thereof.

The invention thus provides a curable coating composition comprising (A) a polymer resin comprising active hydrogen-containing functional group other than carbamate, (B) a curing agent having groups that are reactive with said functional groups on (A), and (C) a reactive additive comprising at least one compound having a molecular weight of from 131 to 2000 and comprising at least one primary carbamate group and at least one alkyl group selected from the group consisting of straight chain alkyl groups of more than 10 carbons, branched alkyl groups of from 5 to 30 carbons, and mixtures thereof, wherein one or both of (A) and (B) comprise groups that are reactive with the primary carbamate group of (C).

The invention further provides methods of making the disclosed reactive additives.

In a first embodiment, the method comprises providing a compound comprising at least one epoxy group and at least one at least one alkyl group selected from the group consisting of straight chain alkyl groups of more than 10 carbons, branched alkyl groups of from 5 to 30 carbons and mixtures thereof, reacting said compound with carbon dioxide so as to produce a carbonate functional compound, and reacting said carbonate functional compound with ammonia so as to produce a carbamate functional reactive additive.

In a second embodiment, the method comprises providing a compound comprising at least one glycol diol and at least one alkyl group selected from the group consisting of straight chain alkyl groups of more than 10 carbons, branched alkyl groups of from 5 to 30 carbons and mixtures thereof, reacting said compound with phosgene or related materials such as triphosgene, and reacting said carbonate functional compound with ammonia or ammonium hydroxide so as to produce a carbamate functional reactive additive.

DETAILED DESCRIPTION OF THE INVENTION

The composition according to the present invention comprises a polymer resin (A) having active hydrogen-containing functional groups other than carbamate. Such polymer resins include, for example, acrylic polymers, modified acrylic polymers, polyesters, polyepoxides, polycarbonates, polyurethanes, polyamides, polyimides, and polysiloxanes, all of which are well known in the art. Preferably, the polymer is an acrylic, modified acrylic or polyester. More preferably, the polymer is an acrylic polymer. Active hydrogen-containing functional groups on polymer resins are well known in the art. Such groups include, for example, hydroxyl groups, amino groups, thiol groups, hydrazide groups, and activated methylene groups.

In one preferred embodiment of the invention, the polymer is an acrylic. The acrylic polymer preferably has a molecular weight of 500 to 1,000,000, and more preferably of 1500 to 50,000. As used herein, "molecular weight" refers to number average molecular weight, which may be determined by the GPC method using a polystyrene standard. Such polymers are well-known in the art, and can be prepared from monomers such as methyl acrylate, acrylic acid, methacrylic acid, methyl methacrylate, butyl methacrylate, cyclohexyl methacrylate, and the like. The active hydrogen functional group, e.g., hydroxyl, can be incorporated into the ester portion of the acrylic monomer. For example, hydroxy-functional acrylic monomers that can be used to form such polymers include hydroxyethyl acrylate, hydroxybutyl acrylate, hydroxybutyl methacrylate, hydroxypropyl acrylate, and the like. Amino-functional acrylic monomers would include t-butylaminoethyl methacrylate and t-butylamino-ethylacrylate. Other acrylic monomers having active hydrogen functional groups in the ester portion of the monomer are also within the skill of the art.

Modified acrylics can also be used as the polymer (A) according to the invention. Such acrylics may be polyester-modified acrylics or polyurethane-modified acrylics, as is well known in the art. Polyester-modified acrylics modified with ε-caprolactone are described in U.S. Pat. No. 4,546,046 of Etzell et al, the disclosure of which is incorporated herein by reference. Polyurethane-modified acrylics are also well known in the art. They are described, for example, in U.S. Pat. No. 4,584,354, the disclosure of which is incorporated herein by reference.

Polyesters having active hydrogen groups such as hydroxyl groups can also be used as the polymer in the composition according to the invention. Such polyesters are well-known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, neopentyl glycol).

Polyurethanes having active hydrogen functional groups are also well known in the art. They are prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylol propane). They can be provided with active hydrogen functional groups by capping the polyurethane chain with an excess of diol, polyamine, amino alcohol, or the like.

The composition of the invention is cured by a reaction of the active hydrogen-functional compound (A) with a component (B) having a plurality of functional groups that are reactive with the active hydrogen groups on component (A). Such reactive groups include active methylol or methylalkoxy groups on aminoplast crosslinking agents or on other compounds such as phenol/formaldehyde adducts, isocyanate groups, siloxane groups, cyclic carbonate groups, and anhydride groups. Examples of (B) compounds include melamine formaldehyde resin (including monomeric or polymeric melamine resin and partially or fully alkylated melamine resin), blocked or unblocked polyisocyanates (e.g., TDI, MDI, isophorone diisocyanate, hexamethylene diisocyanate, and isocyanurate trimers of these, which may be blocked-for example with alcohols or oximes), urea resins (e.g., methylol ureas such as urea formaldehyde resin, alkoxy ureas such as butylated urea formaldehyde resin), polyanhydrides (e.g., polysuccinic anhydride), and polysiloxanes (e.g., trimethoxy siloxane). Aminoplast resin such as melamine formaldehyde resin or urea formaldehyde resin are especially preferred.

Compounds suitable for use as reactive additive (C) are those having at least one primary carbamate group and at least one alkyl radical selected from the group consisting of straight chain alkyl groups of more than 10 carbons, branched alkyl groups of from 5 to 30 carbons, and mixtures thereof.

As used herein, "primary carbamate group" refers to the functional group having the structure

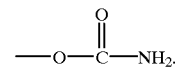

Thus, the primary carbamate group of the invention may be defined as a terminal or pendent carbamate group. Although compounds suitable for use as reactive additive (C) may comprise more than one primary carbamate group, it is most preferred that such compounds have one primary carbamate group.

In addition to the at least one primary carbamate group, compounds suitable for use as reactive additive (C) will further comprise at least one alkyl group selected from the group consisting of branched alkyl groups having from 5 to 30 total carbons, straight chain alkyl groups of more than 10 carbons, and mixtures thereof.

As used herein, the term "branched" refers to both lateral branches and forked branches. Lateral refers to a branch of two small chains at the end atom of a carbon chain. Forked refers to a branch of two small chains in the middle of a carbon chain. For the purposes of the instant invention a carbon chain may be from 1 to 15 carbons, more preferably from 1 to 8 and most preferably from 1 to 3. The total number of carbon atoms in the branched alkyl group is obtained by adding the total number of carbons in the main carbon chain+the number of carbons in all alkyl chains extending from the main carbon chain.

It will be appreciated that the main carbon chain may be from 1 to 25 carbons, preferably from 1 to 10, most preferably from 1 to 4. Most preferably, the main chain will be an aliphatic carbon chain free of unsaturation. Although the at least one branched alkyl group may comprise from 5 to 30 total carbons, more preferably, it will have from 5 to 15 carbons and most preferably from 8 to 12 carbons.

Finally, it will be appreciated that suitable "at least one alkyl groups" for use in reactive additive (C) will be substantially free of functional groups that are reactive with one or more of components (A) and (B). Thus, the at least one alkyl group selected from the group consisting of branched alkyl groups having from 5 to 30 total carbons, straight chain alkyl groups of more than 10 carbons, and mixtures thereof, will be free of hydroxyl groups and the like.

An example of an especially suitable at least one branched alkyl group is

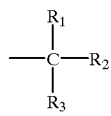

wherein $R_1$, $R_2$, and $R_3$ are alkyl groups of from 1 to 10 carbons each, preferably aliphatic groups of from 1 to 10 carbons. Most preferably, $R_1$, $R_2$, and $R_3$ will total from 8 to 12 carbons with at least one of $R_1$, $R_2$, and $R_3$ being a methyl group.

In another suitable branched alkyl group of the same structure, one of $R_1$, $R_2$, and $R_3$, may be hydrogen, with the other substituent groups being alkyl groups of from 1–10 carbons, preferably aliphatic groups of from 1 to 10. An example of such a group is

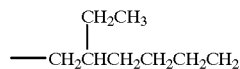

In this instance, the above structure is understood to be an example of lateral branching.

In a particularly preferred embodiment, the at least one branched alkyl group will comprise

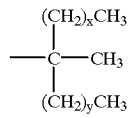

wherein x+y=5 carbons.

Alternatively, the compound suitable for use as reactive additive (C) may include a straight chain alkyl group of more than 10 carbons, preferably more than 15 carbons and most preferably more than 18. Examples of suitable straight chain, aliphatic alkyl groups include 1-eicosanyl, 1-octadecyl, 1-arachidyl, 1-dodecyl, 1-decyl, and 1-octyl, and the like.

It is most preferred that compounds suitable for use as reactive additive (C) include at least one group which is a branched alkyl group such as described above.

Compounds suitable for use as reactive additive (C) may further include heteratoms such as O and N, most preferably O. Such heteratoms may be incorporated in the form of groups such as esters, hydroxyls, ether, carboxyls, mixtures thereof and the like. Preferred are esters, hydroxyls, and mixtures thereof. Most preferably, a compound will comprise at least one hydroxyl group and one ester group in addition to the carbamate functional group and the at least one alkyl group. As indicated above, such heteratoms may not be present in the branched alkyl group nor in the Particularly suitable compounds for use as reactive additive (C) are those having the formula:

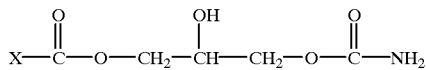

wherein X is a branched alkyl radical of from 5 to 30 total carbons, more preferably from 5 to 15 total carbons and most preferably from 8 to 12 total carbons.

A more preferred compound for use as reactive additive (C) is that having the formula:

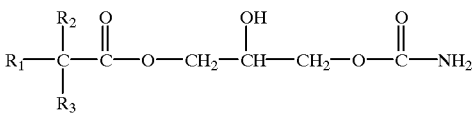

wherein $R_1$, $R_2$, and $R_3$ are each alkyl groups of from 1 to 10 carbons, especially compounds wherein $R_1$, $R_2$, and $R_3$ total from 8 to 12 carbons with at least one of $R_1$, $R_2$, and $R_3$ being a methyl group.

The most preferred compound for use as reactive additive (C) is that having the formula:

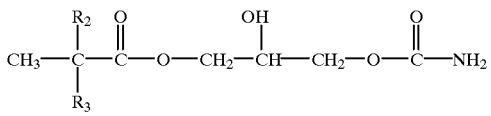

wherein $R_2$ and $R_3$ are respectively $-(CH_2)_x CH_3$ and $-(CH_2)_y CH_3$ wherein x+y=5.

The invention further provides a method of making the reactive additive of the invention. It has been discovered that the most preferred reactive additive of the invention can be made by providing a compound having at least one epoxy group and at least one alkyl group selected from the group consisting of branched alkyl groups of from 5 to 30 total carbons, straight chain alkyl groups of more than 10 carbons, and mixtures thereof. It is preferred that the compound provided will comprise at lest one branched alkyl group of from 5 to 30 total carbons. More preferably the epoxy functional compound will have one epoxy group and a branched alkyl group of from 5 to 15 total carbons and most preferably from 8 to 12 total carbons.

Examples of preferred epoxy functional/branched alkyl group containing compounds are glycidyl ethers, glycidyl esters, and epoxies based on alpha olefins, 2-ethyl hexyl glycidyl ether, and glycidyl esters of the formula:

wherein X is a branched alkyl hydrocarbon radical containing from about 5 to 30 total carbons. More preferably, X is a tertiary aliphatic group of from about 5 to 15 carbons and most preferably from 8 to 12 carbons, such as neopentanoate, neoheptanoate, and neodecanoate. Glycidyl esters of commercially available mixtures of tertiary aliphatic carboxylic acids such as those available from Shell Chemical Company as VERSATIC ACID 911 are particularly preferred as the epoxy group and branched alkyl group containing compound. The glycidyl esters are commercially available from Shell Chemical Company as CARDURA E or GLYDEXX N-10 from Exxon Chemical Company.

The epoxy group and branched alkyl group containing compound is then reacted with carbon dioxide so as to produce a carbonate functional compound. A ring opening catalyst such as triphenyl phosphene or tertiary ammonium salt is normally employed. While the reaction will go under atmospheric pressure, positive pressures are usually used to reduce reaction time.

The resulting carbonate functional compound is subsequently reacted with ammonia or ammonium hydroxide to provide a the primary carbamate functional reactive additive of the invention.

Alternatively, rather than produce a carbonate functional compound, the epoxy could be reacted with water to form alcohols, with subsequent conversion of the alcohols into carbamates via transesterification, urea decomposition and the like.

In a second method of the invention, glycol diols having the same structures of the epoxy functional compounds listed above can be used as a starting material. Such glycol diols must have at least one alkyl group selected from the group consisting of branched alkyl groups of from 5 to 30 total carbons, straight chain alkyl groups of more than 10 carbons, and mixtures thereof. Glycol diol as used herein refers to a diol wherein the two hydroxy groups are on adjacent carbons. Suitable glycol diols may contain other heteroatom groups as discussed above.

The glycol diols are reacted with phosgene or similar materials such as triphosgene. The resulting cyclic carbonate is then reacted as described above to form the primary carbamate functional reactive additive.

Finally, the glycol diols can be directly converted into primary carbamates using techniques such as reaction with urea, HNCO gas, or transesterification with carbamate ester such as methyl carbamate.

The compound (C) will generally have a molecular weight of 131–2000, and preferably from 131–1000 and most preferably from 131 to 500. The glass transition temperature, $T_g$, of components (A), (B), and (C) can be adjusted to achieve a cured coating having the desired $T_g$ for the particular application involved. The compound (C) is preferably used at levels between 3 to 50 percent (based on total resin solids of the coating composition), and more preferably between 5 to 25 percent.

According to the present invention, at least one of components (A) and (B), or both components (A) and (B) must have at least one group thereon that is reactive with the carbamate group(s) on component (C). This is preferably accomplished through the selection of an aminoplast as component (B). Depending on the cure conditions, other compounds identified above as component (B) may also be reactive with the carbamate group(s) on component (C). Component (A) may also contain groups that are reactive with carbamate, such as an acrylic polymer containing isobutoxymethyl acrylamide groups.

A solvent may optionally be utilized in the coating composition used in the practice of the present invention. Although the composition used according to the present invention may be utilized, for example, in the form of substantially solid powder, or a dispersion, it is often desirable that the composition is in a substantially liquid state, which can be accomplished with the use of a solvent. This solvent should act as a solvent with respect to both the carbamate-functional compound (A) as well as the component (B). In general, depending on the solubility characteristics of components (A) and (B), the solvent can be any organic solvent and/or water. In one preferred embodiment, the solvent is a polar organic solvent. More preferably, the solvent is a polar aliphatic solvents or polar aromatic solvents. Still more preferably, the solvent is a ketone, ester, acetate, aprotic amide, aprotic sulfoxide, or aprotic amine. Examples of useful solvents include methyl ethyl ketone, methyl isobutyl ketone, m-amyl acetate, ethylene glycol butyl ether-acetate, propylene glycol monomethyl ether acetate, xylene, N-methylpyrrolidone, or blends of aromatic hydrocarbons. In another preferred embodiment, the solvent is water or a mixture of water with small amounts of co-solvents.

The coating composition used in the practice of the invention may include a catalyst to enhance the cure reaction. For example, when aminoplast compounds, especially monomeric melamines, are used as component (B), a strong acid catalyst may be utilized to enhance the cure reaction. Such catalysts are well known in the art and include, for example, p-toluenesulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

In a preferred embodiment of the invention, the solvent is present in the coating composition in an amount of from about 0.01 weight percent to about 99 weight percent, preferably from about 10 weight percent to about 60 weight percent, and more preferably from about 30 weight percent to about 50 weight percent.

Coating compositions can be coated on the article by any of a number of techniques well known in the art. These include, for example, spray coating, dip coating, roll coating, curtain coating, and the like. For automotive body panels, spray coating is preferred.

Any additional agent used, for example, surfactants, fillers, stabilizers, wetting agents, dispersing agents, adhesion promoters, UV absorbers, HALS, etc. may be incorporated into the coating composition. While the agents are well known in the prior art, the amount used must be controlled to avoid adversely affecting the coating characteristics.

The coating composition according to the invention is preferably utilized in a high-gloss coating and/or as the clearcoat of a composite color-plus-clear coating. High-gloss coatings as used herein are coatings having a 20° gloss (ASTM D523-89) or a DOI (ASTM E430-91) of at least 80.

When the coating composition of the invention is used as a high-gloss pigmented paint coating, the pigment may be any organic or inorganic compounds or colored materials, fillers, metallic or other inorganic flake materials such as mica or aluminum flake, and other materials of kind that the art normally names as pigments. Pigments are usually used in the composition in an amount of 1% to 100%, based on the total solid weight of components A, B and C (i.e., aP:B ratio of 0.1 to 1).

When the coating composition according to the invention is used as the clearcoat of a composite color-plus-clear coating, the pigmented basecoat composition may any of a number of types well known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of cross-linkable functional groups. Such groups include, for example, hydroxy, isocyanate, amine, epoxy, acrylate, vinyl, silane, and acetoacetate groups. These groups may be masked or blocked in such a way so that they are unblocked and available for the cross-linking reaction under the desired curing conditions, generally elevated temperatures. Useful cross-linkable functional groups include hydroxy, epoxy, acid, anhydride, silane, and acetoacetate groups. Preferred cross-linkable functional groups include hydroxy functional groups and amino functional groups.

Basecoat polymers may be thermoplastic, self-cross-linkable, or may require a separate cross-linking agent that is reactive with the functional groups of the polymer. When the polymer comprises hydroxy functional groups, for example, the cross-linking agent may be an aminoplast resin, isocyanate and blocked isocyanates (including isocyanurates), and acid or anhydride functional cross-linking agents.

The coating compositions described herein are preferably subjected to conditions so as to cure the coating layers. Although various methods of curing may be used, heat curing is preferred. Generally, heat curing is effected by exposing the coated article to elevated temperatures provided primarily by radiative heat sources. Curing temperatures will vary depending on the particular blocking groups used in the cross-linking agents, however they generally range between 93° C. and 177° C. The compounds (C) according to the present invention are reactive even at relatively low cure temperatures. Thus, in a preferred embodiment, the cure temperature is preferably between 115° C. and 150° C., and more preferably at temperatures between 115° C. and 138° C. for a blocked acid catalyzed system. For an unblocked acid catalyzed system, the cure temperature is preferably between 82° C. and 99° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following examples. All parts and percentages are by weight unless otherwise specified.

EXAMPLE 1

Preparation of a Preferred Reactive Additive (c).

Part (A)

Preparation of Cyclic Carbonate of the Glycidyl Ester of Neodecanoic Acid

A mixture of 16428 parts of Glydexx N-10 (glycidyl ester of neodecanoic acid, commercially available from Exxon Chemical Company) and 125.5 parts of tetrabutyl ammonium bromide was heated under $CO_2$ pressure (6.5 bars) to 120° C. The reaction mixture was held at 120° C. under pressure until the reaction was complete. The product mixture was then cooled and excess carbon dioxide removed.

Part (B1)

Preparation of the Beta Hydroxy Carbamate

Ammonia gas was added to a mixture of 24290 parts of the product of Part (A) and 16192 parts of methanol. When the ring opening of the cyclic carbonate was complete, the methanol and excess ammonia was removed by vacuum.

Part (B2)

Alternative Preparation of the Beta Hydroxy Carbamate

To a solution of 200 parts of concentrated ammonium hydroxide was slowly added 700 parts of the cyclic carbonate of Neodecanoic acid glycidyl ester (part A). Once the reaction was complete, the excess water and ammonium hydroxide was removed by vacuum distillation.

EXAMPLE 2

Incorporation of the Product of Example 1, Part (B) into a Binder Composition

A solution of 1121 parts of deionized water and 25.5 parts of ABEX EP110 (commercially available from Rhodia Inc.) was heated to 82° C. under an inert atmosphere. A mixture of 306.5 parts of deionized water, 102.2 parts of ABEX EP 110, 729.1 parts of butyl acrylate, 109.1 parts of hydroxyethyl methacrylate, 85 parts of hydroxypropyl methacrylate, 317.6 parts of styrene, 25.6 parts of hexanediol diacrylate, 93,3 parts of methyl methacrylate, 25.6 parts of methacrylic acid, 32 parts of acrylic acid, 12.7 parts of 1-octaine thiol, 3.87 parts of ammonium persulfate and 70.8 parts of the product of Example 1, Part (B) was made and added to the heated solution over a period of about two hours. The resulting reaction mixture was held at 82° C. for two hours. The reaction mixture was then cooled to less than 40° C. and 7.6 parts of aminopropanol, 6.4 parts of Nuosept® 95 (commercially available from Creanova Inc.) and 32.4 parts of deionized water was added. The final resin emulsion was free of coagulum and had a nonvolatile of 39.1, and a pH of 5.61.

EXAMPLE 3

Preparation and Evaluation of Coating Compositions Prepared According to the Invention vs. Prior Art Compositions Clearcoat coating compositions with (Coating A) and without (Coating B) the reactive additive (C) were prepared according to the following table.

| Component | Coating A | Coating B |
|---|---|---|
| Reactive additive-Ex 1B1 | 32.94 | 0.00 |
| Resin-Ex 3A | 53.13 | 107.42 |
| Crosslinking Agent[1] | 28.47 | 27.75 |
| UV Absorber[2] | 1.00 | 1.00 |
| UV Absorber[3] | 15.71 | 15.71 |
| HALS[4] | 6.00 | 6.00 |
| Flow Agent[5] | 0.80 | 0.80 |

[1]Resimene 747, commercially available from Solutia of St Louis, MO.
[2]A UV absorber, commercially available from Ciba Geigy.
[3]A UV absorber, commercially available from Ciba Geigy.
[4]A hindered amine light stabilizer, commercially available from Ciba Geigy.

| | | |
|---|---|---|
| DDBSA[6] | 4.00 | 4.00 |
| EXXATE 1000[7] | 7.00 | 7.00 |
| MIAK[8] | 5.01 | 10.01 |

The viscosity of Coating A was 34 seconds on a #4 Ford cup @ 80° F. The theoretical weight percent nonvolatile of Coating A was 64.91%. The viscosity of Coating B was 34 seconds on a #4 Ford cup @ 80° F. The theoretical weight percent nonvolatile of Coating B was 51.80%. The actual weight percent nonvolatile of Coating B was 55.65%.

Accordingly, it can be seen that significant improvements in % nonvolatile are obtained with the use of the reactive additive (C).

We claim:
1. A curable coating composition comprising
   (A) a polymer resin comprising active hydrogen-containing functional group other than carbamate,
   (B) a curing agent having groups that are reactive with said functional groups on (A), and
   (C) a reactive additive comprising at least one compound having a molecular weight of from 131 to 2000 and comprising at least one β-hydroxy primary carbamate group and at least one alkyl group selected from the group consisting of branched alkyl groups of from 5 to 30 carbons, straight chain alkyl groups of more than 10 carbons, and mixtures thereof, wherein one or both of (A) and (B) comprise groups that are reactive with the primary carbamate group of (C).

2. The curable coating composition of claim 1 wherein the reactive additive (C) has only one carbamate group.

3. The curable coating composition of claim 1 wherein the at least one alkyl group is a branched allyl group of from 8 to 12 carbons.

4. The curable coating composition of claim 3 wherein the at least one alkyl group is a branched alkyl group of at least 10 carbons.

5. A curable coating composition comprising
(A) a polymer resin comprising active hydrogen-containing functional group other than carbamate,
(B) a curing agent having groups that are reactive with said functional groups on (A), and
(C) a reactive additive comprising at least one compound having a molecular weight of from 233 to 583 and having the formula:

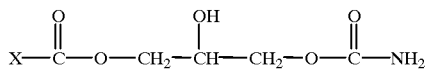

wherein X is a branched alkyl group of from 5 to 30 carbons, and one or both of (A) and (B) comprise groups that are reactive with the primary carbamate group of (C).

6. The curable coating composition of claim 5 wherein the reactive additive (C) is only one carbamate compound.

7. The curable coating composition of claim 5 wherein X is

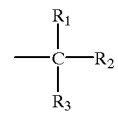

wherein one of $R_1$, $R_2$ and $R_3$ is hydrogen and each of the remaining $R_1$, $R_2$ and $R_3$ is an alkyl group of from 1 to 10 carbons.

8. The curable coating composition of claim 7 wherein $R_1$, $R_2$, and $R_3$ total from 8 to 12 carbons with at least one of $R_1$, $R_2$, and $R_3$ being a methyl group.

9. The curable coating composition of claim 7 wherein one of $R_1$, $R_2$, and $R_3$ is hydrogen.

10. A curable coating composition comprising
(A) a polymer resin comprising active hydrogen-containing functional group other than carbamate,
(B) a curing agent having groups that are reactive with said functional groups on (A), and
(C) a reactive additive comprising at least one compound having a molecular weight of from 131 to 2000 and having the formula:

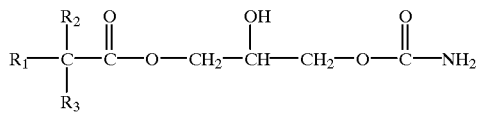

wherein $R_1$, $R_2$, and $R_3$ are each alkyl groups of from 1 to 10 carbons, and one or both of (A) and (B) comprise groups that are reactive with the primary carbamate group of (C).

11. The curable coating composition of claim 10 wherein $R_1$, $R_2$, and $R_3$ total from 8 to 12 carbons with at least one of $R_1$, $R_2$, and $R_3$ being a methyl group.

* * * * *